US00PP11945P2

(12) United States Plant Patent
Booman

(10) Patent No.: US PP11,945 P2
(45) Date of Patent: Jun. 19, 2001

(54) BEGONIA PLANT NAMED 'SAVANNAH PINK PARFAIT'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,787

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Savannah Pink Parfait', charactized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Savannah Pink Parfait'.

The new Rex Begonia was discovered and selected by the Inventor in a controlled environment in Vista, Calif., in August, 1995, within a large group of seedling progeny from multiple crossings of unidentified selections of *Begonia rex* hybrids.

The selection of this plant was based on its uniform growth habit, moderate plant vigor, and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Savannah Pink Parfait' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Savannah Pink Parfait'. These characteristics in combination distinguish 'Savannah Pink Parfait' as a new and distinct Rex Begonia:

1. Uniform growth habit.
2. Moderate plant vigor.
3. Does not require winter dormancy.
4. Interesting and attractive leaf coloration and pattern.

In side-by-side comparsions conducted by the Inventor in Vista, Calif., plants of the new Rex Begonia differ from plants of the nonpatented cultivar 'Merry Christmas Corkscrew' in the following characteristics:

1. Plants of the new Rex Begonia grow more rapidly than plants of the cultivar 'Merry Christmas Corkscrew'.

2. Leaves of plants of the new Rex Begonia are flatter and brighter in color than leaves of plants of the cultivar 'Merry Christmas Corkscrew'.
3. Leaves of plants of the new Rex Begonia do not have a "corkscrew" formation whereas leaves of plants of the cultivar 'Merry Christmas Corkscrew' have a "corkscrew" formation.
4. Plants of the new Rex Begonia do not require a winter dormancy period whereas plants of the cultivar 'Merry Christmas Corkscrew' do require a winter dormancy period.

In side-by-side comparisons conducted by the Inventor in Vista, Calif., plants of the new Rex Begonia differ from plants of the nonpatented cultivar 'Lillium' in the following characteristics:

1. Plants of the new Rex Begonia are more compact, denser and more freely flowering than plants of the cultivar 'Lillium'.
2. Plants of the new Rex Begonia have more brightly colored leaves than plants of the cultivar 'Lillium'.
3. Plants of the new Rex Begonia do not require a winter dormancy period whereas plants of the cultivar 'Lillium' do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Savannah Pink Parfait'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the Spring in Vista, Calif., under conditions which approximate commercial practice. Plants used for this description were grown in 15-cm containers for about 3 months.

Botanical classification: *Begonia rex* hybrid cultivar 'Savannah Pink Parfait'.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days to 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 21 cm.

*Plant width.*—About 48 cm.

*Leaves.*—Arrangement: Simple. Length: Petiole to apex: About 15 cm. Base to apex: About 19 cm. Width: About 12.5 cm. Shape: Oblique to elliptical. Apex: Acute. Base: Asymmetrically cordate. Margin: Pectinate; irregularly undulate. Texture: Leathery, rugose; pubescence on lower surface veins. Color: Young foliage, upper surface: Margin: Very thin border, 187A. Central venal areas: 147A to 202A. Blade to margin: Iridescent, 191C, with flush of metallic 186C and 186A towards center. Antemarginal: Small irregular blotches of 147A. Young foliage, lower surface: Margin: 183A. Central venal areas: Close to 185A. Background: Uniformly green, 147C. Mature, fully expanded, foliage, upper surface: Margin: Thin border, 186A. Central venal areas: Clearly marked 200A. Blade to margin: Iridescent, 191C, with flush of metallic 185B to 186B extending to center. Antemarginal: Blotches of 147A and some irregular blotches of 147C with age. Veins: 166A. Mature, fully expanded, foliage, lower surface: Margin: 187A. Central venal area: 183A. Background: Hint of 148C. Veins: 183B; reticulate.

*Petioles.*—Length: About 14 cm. Diameter: About 6.5 mm. Shape: Longitudinally grooved. Texture: Pubescent. Color: Slightly translucent, 178A.

*Stipules.*—Length: About 15 mm. Diameter at base: About 5 mm. Shape: Subulate, deltoid. Color: Close to 184A.

Flower description:

*Flowering habit.*—Male flowers, single with one whorl of four tepals. Female flowers, semi-double with three tepals interior to outer whorl of five tepals. Usually about three flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 3.4 cm. Depth (height): About 1.6 cm. Aspect: Drooping about 45° from vertical. Fragrance: None.

*Flower buds.*—Shape: Ovoid; bulbous with marginal lip. Length: About 1.2 cm. Diameter: About 1 cm. Color: 55A and 52A.

*Tepals.*—Arrangement: Rosette. Length: About 1.6 cm. Width: About 1.2 cm. Shape: Ovate with obtuse apex. Margin: Entire. Texture: Smooth, waxy; iridescent, translucent. Color: When opening, upper surface: 55A. When opening, lower surface: 52A. Fully opened, upper surface: 55A to 55B. Fully opened, lower surface: 52A to 52B.

*Peduncles.*—Angle: About 20° from vertical. Length: About 2.5 cm. Diameter: About 2 mm. Strength: Firm. Texture: Smooth, waxy. Color: 178A.

*Pedicels.*—Angle: About 40° from vertical. Length: About 1.5 cm. Diameter: About 1.5 mm. Strength: Moderate; flexible. Texture: Smooth, waxy. Color: 51B.

*Reproductive organs.*—Male flowers: Stamen quantity: About 70; globose mass. Anther shape: Rhomboidal; lower sides curved inwardly. Anther length: About 2 mm. Filament length: About 1 mm. Anther color: 168C. Pollen: Not observed. Female flowers: Pistil length: About 1.7 cm. Stigma shape: Funnel; bilobate. Stigma color: 163A. Ovary: Inferior; three-winged; one large top wing and two lower wings, both surfaces; 51A to 47C.

Disease resistance: Resistance to diseases common to Rex Begonia has not been determined.

Seed production: Seed production has not been observed.

It is claimed:

1. A new and distinct cultivar of Rex Begonia plant named 'Savannah Pink Parfait', as illustrated and described.

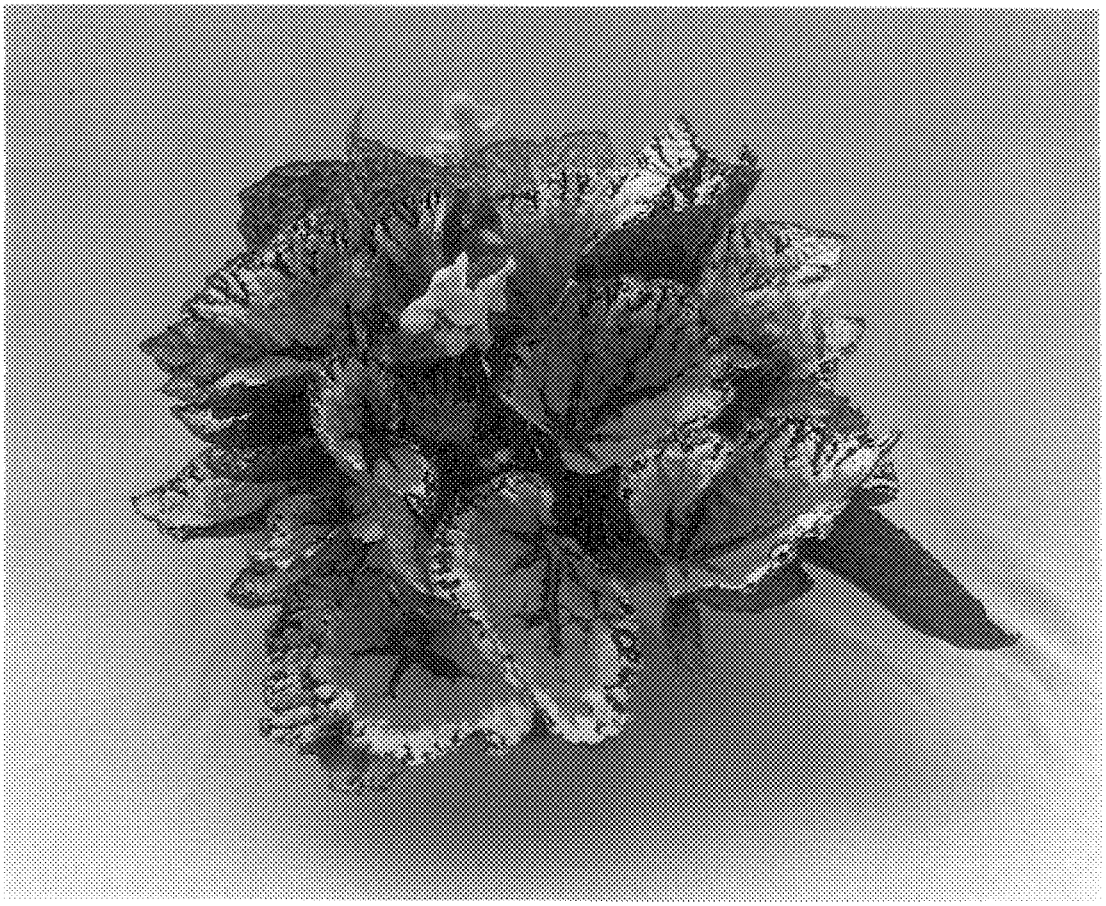

* * * * *